United States Patent
Falini et al.

(10) Patent No.: US 11,337,983 B2
(45) Date of Patent: *May 24, 2022

(54) DACTINOMYCIN COMPOSITIONS AND METHODS FOR THE TREATMENT OF ACUTE MYELOID LEUKEMIA

(71) Applicants: Brunangelo Falini, Perugia (IT); Maria Paola Martelli, Perugia (IT)

(72) Inventors: Brunangelo Falini, Perugia (IT); Maria Paola Martelli, Perugia (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/418,374

(22) Filed: May 21, 2019

(65) Prior Publication Data

US 2019/0314380 A1 Oct. 17, 2019

Related U.S. Application Data

(63) Continuation of application No. 15/759,442, filed as application No. PCT/EP2016/071599 on Sep. 13, 2016, now Pat. No. 10,335,416.

(60) Provisional application No. 62/218,433, filed on Sep. 14, 2015.

(51) Int. Cl.
*A61K 31/538* (2006.01)
*A61P 35/02* (2006.01)
*A61K 9/00* (2006.01)

(52) U.S. Cl.
CPC .......... *A61K 31/538* (2013.01); *A61K 9/0019* (2013.01); *A61P 35/02* (2018.01)

(58) Field of Classification Search
CPC ...... A61K 31/538; A61K 9/0019; A61P 35/02
See application file for complete search history.

(56) References Cited

U.S. PATENT DOCUMENTS

| | | | |
|---|---|---|---|
| 4,522,811 | A | 6/1985 | Eppstein et al. |
| 10,335,416 | B2 | 7/2019 | Falini et al. |
| 2006/0111358 | A1 | 5/2006 | De Bont et al. |
| 2007/0010465 | A1 | 1/2007 | Sikic et al. |

FOREIGN PATENT DOCUMENTS

| | | |
|---|---|---|
| WO | WO 2004/032935 A1 | 4/2004 |
| WO | WO 2011/157802 A1 | 12/2011 |
| WO | WO 2015/101618 A1 | 7/2015 |

OTHER PUBLICATIONS

Cosmegen (https://www.accessdata.fda.gov/drugsatfda_docs/label/2012/050682s029s030lbl.pdf, 2012). (Year: 2012).*
Etsey (Leukemia, 2012, 26, 861-869). (Year: 2012).*
Dawson (Haematologica, 2007, 92, 996-997) (Year: 2007).*
Burger, K. et al. "Chemotherapeutic drugs inhibit ribosome biogenesis at various levels" The Journal of Biological Chemistry, 2010, vol. 285, p. 12416-12425.
Cosmegen® for Injection (dactinomycin for injection) (Actinomycin D), https://www.accessdata.fda.gov/drugsatfda_docs/label/2012/050682s029s030lbl.pdf, 2012.
Falini, B. et al. "Cytoplasmic nucleophosmin in acute myelogenous leukemia with a normal karyotype" The New England Journal of Medicine 2005, vol. 352, No. 3, p. 254-66.
Falini, B. et al. "Acute myeloid leukemia with mutated nucleophosmin (NPM1): any hope for a targeted therapy?" Blood Reviews, 2011, vol. 25, p. 247-254.
Falini, B. et al. "Dactinomycin in NPM1-Mutated Acute Myeloid Leukemia" The New England Journal of Medicine, 2015, vol. 373, No. 12, p. 1180-1182.
"Genomic and epigenomic landscapes of adult de novo acute myeloid leukemia" Cancer Genome Atlas Research Network, The New England Journal of Medicine, 2013, vol. 368, p. 2059-2074.
Osathanondh, R. et al. "Actinomycin D as the primary agent for gestational trophoblastic disease" Cancer, 1975, vol. 36, p. 863-866.
van der Helm et al. "Azacitidine might be beneficial in a subgroup of older AML patients compared to intensive chemotherapy: a single centre retrospective study of 227 consecutive patients" Journal of Hematology & Oncology, 2013, vol. 6, p. 29.
EudraCT No. 2014-000693-18, EU Clinical Trials Register, 2014, 5 pages.
The Journal of Pediatric Practice, 2003, vol. 66, No. 5, pp. 854-858. (English translation included).

* cited by examiner

*Primary Examiner* — Umamaheswari Ramachandran
(74) *Attorney, Agent, or Firm* — Cooley LLP

(57) ABSTRACT

The disclosure provides a method for treating NPM1-mutated acute myeloid leukemia (AML) by administration of a composition comprising dactinomycin.

34 Claims, 7 Drawing Sheets

DACTINOMYCIN COMPOSITIONS AND METHODS FOR THE TREATMENT OF ACUTE MYELOID LEUKEMIA

RELATED APPLICATIONS

This application is a continuation of U.S. application Ser. No. 15/759,442, filed Mar. 12, 2018, now U.S. Pat. No. 10,335,416, which is a U.S. National Phase application, filed under 35 U.S.C. § 371 (c), of International Application No. PCT/EP2016/071599, filed on Sep. 13, 2016, which claims priority to, and the benefit of, U.S. Provisional Application No. 62/218,433, filed Sep. 14, 2015. The contents of each of which are incorporated herein by reference in their entireties.

FIELD OF THE DISCLOSURE

The disclosure is directed to the field of molecular biology as it relates to genetic screening, diagnosing and treating patients having cancer.

BACKGROUND

NPM1-mutated acute myeloid leukemia (AML) is a distinct leukemia entity that accounts for one third of cases of AML in adults. There is a long-felt yet unmet need for effective treatments for AML, including NPM1-mutated AML.

SUMMARY

The disclosure provides compositions and methods for the treatment of AML, and, in particular, the treatment of NPM1-mutated AML that addresses the underlying pathology in addition to the clinical symptoms of AML.

The disclosure provides a method for treating acute myeloid leukemia (AML) in a subject in need thereof comprising administering to the subject a therapeutically-effective amount of a composition comprising Dactinomycin. In preferred methods, the AML is NPM1-mutated AML. In certain embodiments, the NPM1-mutated AML does not have FLT3 internal tandem duplication repeats.

Dactinomycin compositions of the disclosure may further comprise a pharmaceutically-acceptable carrier.

According to the methods of the disclosure, a therapeutically-effective amount of the composition is between 1 and 30 µg/kg/day or between 10 and 20 µg/kg/day, inclusive of the endpoints. Low dosages are effective over longer periods of time. For example, a dose of 1 µg/kg/day may be used for a long-term daily and/or maintenance dosage to prevent relapse. High dosages may be used safely for shorter periods of time. For example, 30 µg/kg/day may be used for one day when followed by a decreased dosage or a period of non-treatment, for example, a period of two-weeks of non-treatment between single-day treatment cycles. Alternatively, a high dose may be used to quickly increase or spike the blood plasma levels above a minimum effective threshold when followed the next day or following a non-treatment period with a lower dose to maintain blood plasma concentration of the dactinomycin. In certain embodiments of the methods of the disclosure, the therapeutically-effective amount of the composition is about 15 µg/kg/day or is 15 µg/kg/day. Alternatively, the therapeutically-effective amount of the composition is about 12.5 µg/kg/day or is 12.5 µg/kg/day. The therapeutically-effective amount of the composition may be administered once per day or at least once per day.

Therapeutically-effective amounts of a Dactinomycin composition of the disclosure may be administered for at least one cycle. In certain embodiments of the methods of the disclosure, the therapeutically-effective amount of the composition is administered for at least two cycles. In certain embodiments of the methods of the disclosure, the therapeutically-effective amount of the composition is administered for six cycles. In certain embodiments, a cycle may comprise or consist of 5 consecutive days of treatment. The interval between two treatment cycles, or intercycle period, is at least two weeks. The interval between two treatment cycles, or intercycle period, may be at least four weeks.

Methods of the disclosure may further comprise the step of administering a blood transfusion to the subject. In certain embodiments, the Dactinomycin composition and the blood transfusion may be administered simultaneously. Alternatively, the Dactinomycin composition and the blood transfusion may be administered sequentially. In certain embodiments, the Dactinomycin composition is administered before the blood transfusion. For example, a cycle of administration of the Dactinomycin composition may be completed and the blood transfusion may be administered after the cycle of Dactinomycin therapy or between two cycles of Dactinomycin therapy.

Dactinomycin compositions of the disclosure may be administered systemically by intravenous injection or infusion. Alternatively, or in addition, Dactinomycin compositions of the disclosure may be administered systemically by any route known in the art.

Subjects of the disclosure may be at least 50, 60, or 70 years of age. In certain embodiments, subjects of the disclosure may have failed to respond to one or more cancer therapies prior to administration of a Dactinomycin composition of the disclosure. For example, a subject may not have responded to treatment with azacitdine prior to administration of a Dactinomycin composition of the disclosure. Subjects of the disclosure may have relapsed following one or more cancer therapies prior to administration of a Dactinomycin composition of the disclosure.

According to methods of the disclosure, Dactinomycin may be administered as a preferred, frontline therapy, for subjects having newly diagnosed and/or previously untreated AML who are unfit for intensive chemotherapy or the elderly (i.e. subjects 60 year of age or older). Subjects who may be unfit for intensive chemotherapy include, but are not limited, to subject who have a compromised immune system, a blood disorder, an intestinal disorder, or an infection.

According to methods of the disclosure, a subject treated with a Dactinomycin composition may subsequently enter remission. As used herein, the term remission includes morphological and/or molecular remission.

DETAILED DESCRIPTION

Figure 1:
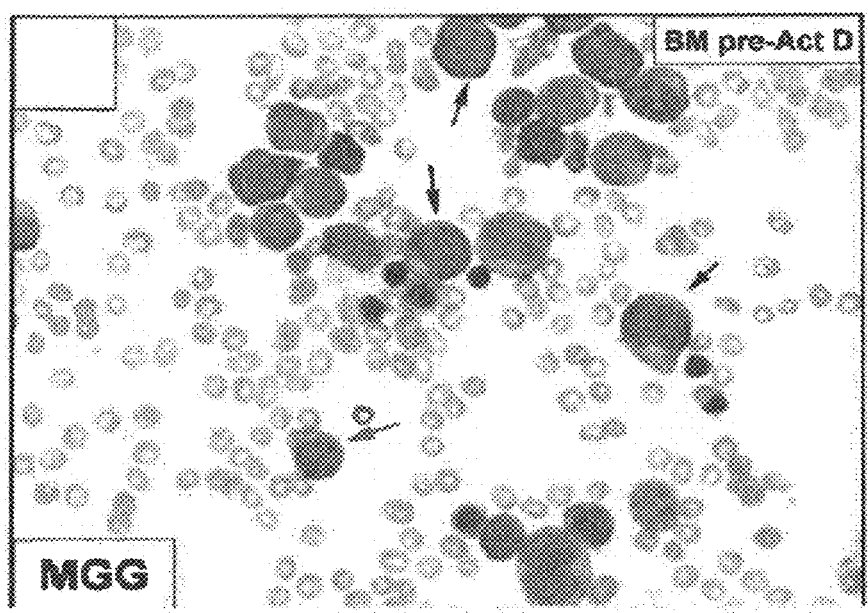
FIG. 1 is a May-Grünwald-Giemsa (MGG) staining of bone marrow aspirate before dactinomycin therapy that shows marked infiltration by leukemic blasts (arrows).
Figure 2:
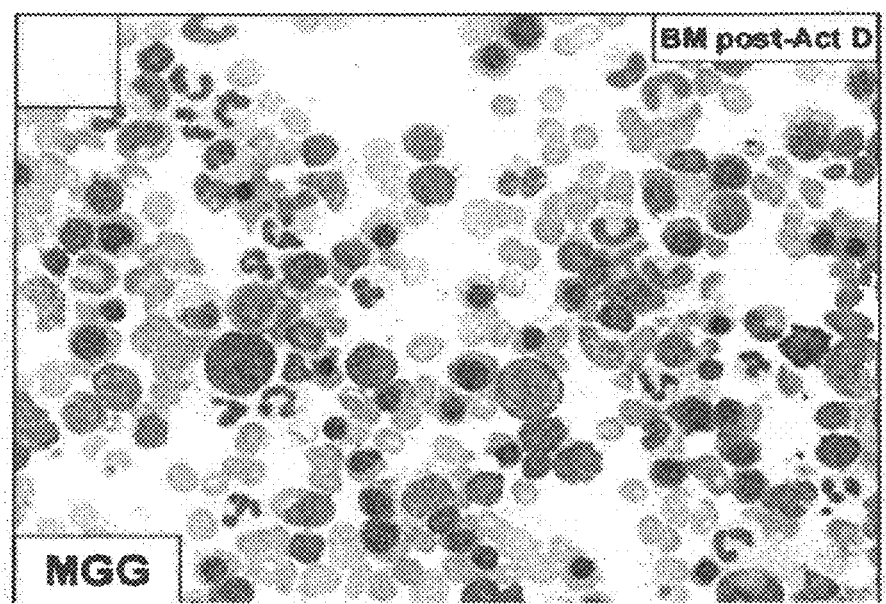
FIG. 2 is a MGG staining of bone marrow aspirate after two cycles of dactinomycin that shows trilineage hemopoiesis with myelodysplastic features and less than 5% leukemic blasts (hematologic complete remission).
Figure 3:
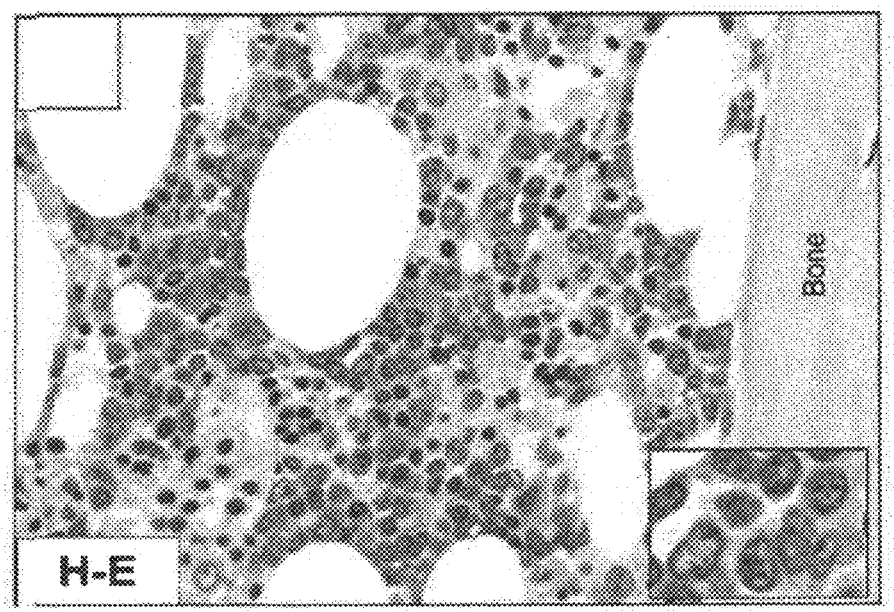
FIG. 3 is a hematoxylin and eosin staining of a trephine biopsy sample of bone marrow before treatment that shows marked infiltration by leukemic cells; the inset shows the blasts at a higher magnification.
Figure 4:
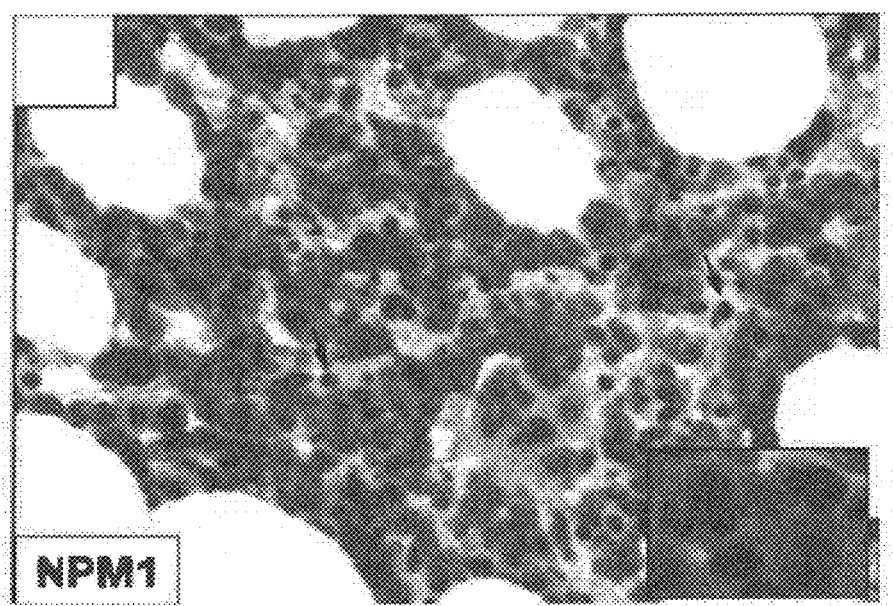
FIG. 4 is an immunostaining with anti-NPM1 monoclonal antibody of bone marrow trephine before treatment that shows strong aberrant cytoplasmic expression of nucleophosmin by leukemic cells (details in inset). Arrows indicate occasional residual normal hematopoietic cells with nucleus-restricted positivity for NPM1.
Figure 5:
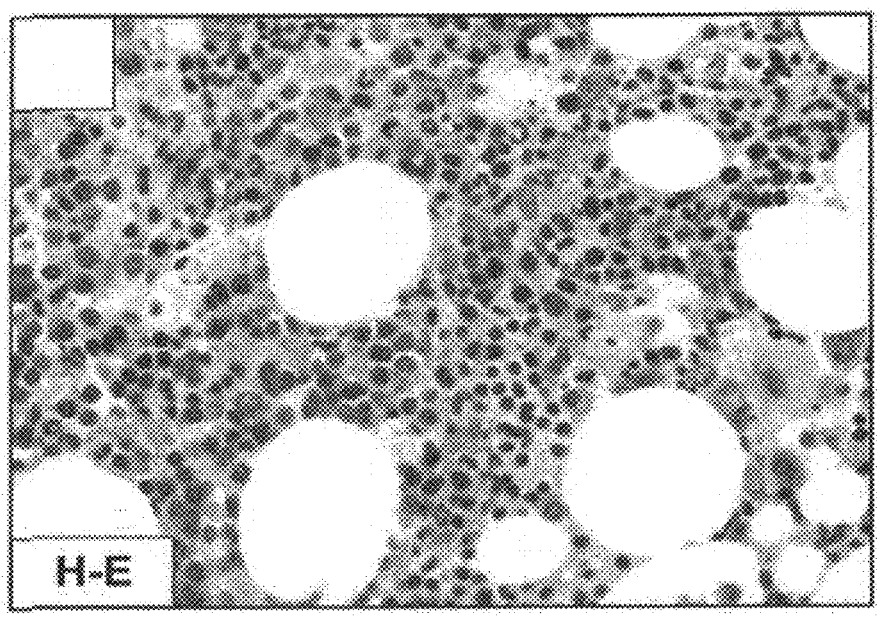
FIG. 5 is an immunostaining with anti-NPM1 monoclonal antibody of bone marrow trephine before treatment that shows strong aberrant cytoplasmic expression of nucleophosmin by leukemic cells (details in inset). Arrows indicate occasional residual normal hematopoietic cells with nucleus-restricted positivity for NPM1.
Figure 6:
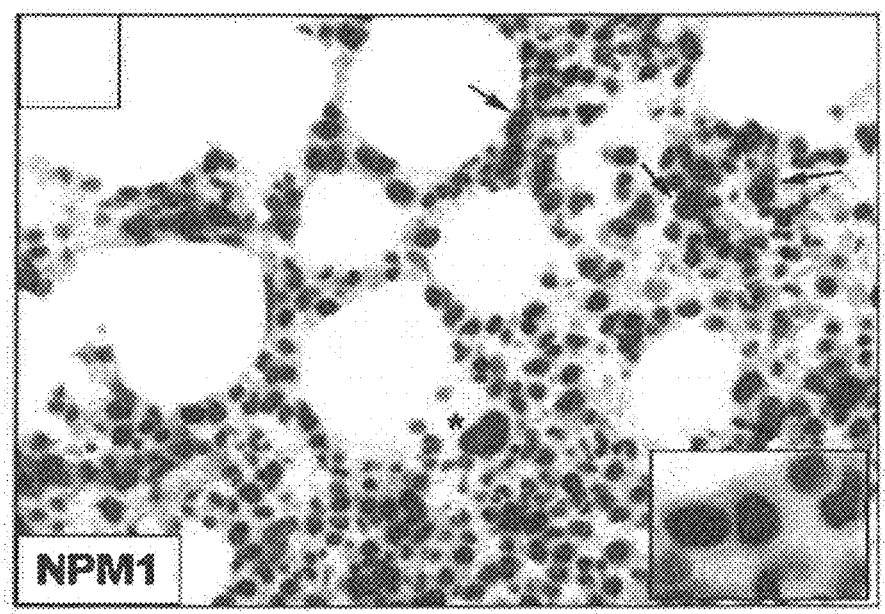
FIG. 6 is an immunostaining with anti-NPM1 monoclonal antibody of normal hematopoietic cells after two cycles of dactinomycin that show nucleus-restricted positivity for NPM1 (details in inset), with the exception of cells in mitosis (arrows). The asterisk indicates NPM1 nuclear staining of a normal megakaryocyte.

NPM1-mutated acute myeloid leukemia (AML) is a distinct leukemia entity that accounts for one third of cases of AML in adults. NPM1 is a crucial protein for normal nucleolar integrity and function. Because it contains a low level of non-mutant NPM1 (owing to haploinsufficiency and cytoplasmic retention of nonmutant NPM1 by the NPM1 mutant), the nucleolus of NPM1-mutated AML cells may be vulnerable to drugs that trigger a nucleolar stress response. Either p53-dependent or p53-independent responses to nucleolar stress have been described. Importantly, the p53-mediated nucleolar stress response is retained in NPM1-mutated AML because NPM1-mutated AML cells lack p53 mutations or deletions.

Among potentially active drugs, the disclosure focuses on dactinomycin because it induces nucleolar stress by interfering with ribosome biogenesis through inhibition of RNA polymerase I. Dactinomycin is active in Wilms' tumor and some other tumors, however, the disclosure describes the first study on dactinomycin use in AML.

Acute Myeloid Leukemia (AML)

Acute Myeloid Leukemia (AML) is the most common name for a condition that is alternatively referred to as acute myelocytic leukemia, acute myelogenous leukemia, acute granulocytic leukemia, or acute non-lymphocytic leukemia.

AML initially develops in the bone marrow, however, AML cells quickly progress into the blood. Once present in the blood of a subject, the cancerous cells may spread to every part of the body, including, but not limited to, the lymph nodes, liver, spleen, central nervous system (brain and/or spinal cord), cutis and testicles.

As an acute form of leukemia, the cancer cells are immature blood cells with stem cell-like qualities that, under normal conditions, rapidly divide to provide a number of blood cell types. When these cells undergo an oncogenic transformation, this rapid division produces cancer cells at a faster rate than a cancer affecting a mature and/or terminally differentiated cell type.

As a myeloid form of leukemia, cancer cells transform from stem-like myeloid cells that, under normal conditions, divide to generate cells that differentiate into red blood cells, white blood cells, and the megakaryocytes that generate platelets. When these cells undergo an oncogenic transformation, immature myeloid cells divide rapidly without subsequently producing the numbers and/or proportions of red blood cells, white blood cells, and platelets that should normally populate the circulating blood. Consequently, under oncogenic conditions, myeloid cells divide and aggregate in the bones, the increased production of these cells competing for resources with and interrupting the not function of healthy, non-cancerous, cells in the bone marrow. Moreover, under oncogenic conditions, myeloid cells produce an insufficient amount of red blood cells to carry normal levels of oxygen through the blood to one or more organs, insufficient amount of white blood cells to mount an adequate immune response to infection, and/or insufficient amount of platelets to facilitate blood clotting.

Subjects of the disclosure may present one or more risk factors for developing AML. Exemplary risk factors include, but are not limited to, personal and/or family history of cancer, increasing age, being male, prior treatment with chemotherapy and/or radiation, exposure to radiation (including survivors of nuclear reactor accidents), exposure to hazardous chemicals (including, for example, benzene), past or current smoking habit, exposure to secondhand smoke, personal history of other blood disorders (including, for example, myelodysplasia, polycythemia vera and/or thrombocythemia), genetic disorders (including, for example, Down syndrome). Although subjects of the disclosure may be any gender, subjects who are genetically male have an increased risk of developing AML compared to those subjects who are genetically female. Although subjects of the disclosure may be any age, those subjects who are at least 40, at least 50, at least 60, at least 70, at least 80, or at least 90 have a greater risk of developing AML compared to younger subjects.

Subjects of the disclosure may present one or more signs or symptoms of AML, including, but not limited to, fever, bone pain, lethargy and/or fatigue, shortness of breath, pale skin, frequent infections, easy bruising, unusual bleeding (from, for example, nose and gums, and/or diminished or insufficient blood clotting).

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

According to methods of the disclosure, Dactinomycin may be administered as a preferred, frontline therapy, for subjects having newly diagnosed and/or previously untreated AML who are unfit for intensive chemotherapy or the elderly (i.e. subjects 60 year of age or older). Subjects who may be unfit for intensive chemotherapy include, but are not limited, to subject who have a compromised immune system, a blood disorder, an intestinal disorder, or an infection.

Subjects of the disclosure may have been treated for AML with another therapy and may have been resistant to that therapy or may not have shown any improvement as a result of that therapy. Thus, subjects of the disclosure include those individuals who have failed one or more therapies prior to treatment with dactinomycin according to the methods of the disclosure.

Treating AML can result in a partial or a complete hematological remission. A complete hematological remission is defined as a reduction of leukemic cells to <5% of bone marrow cells at morphological examination of bone marrow smears and/or sections. A partial hematological remission is defined as a reduction of leukemic cells to >5%, but less than an initial percentage of bone marrow cells, determined by a morphological examination of bone marrow smears and/or sections. The initial percentage of leukemic cells among bone marrow cells may be determined at the time of diagnosis and/or initiation of treatment. A reduction of that initial percentage may be determined at any point during or following the completion of treatment.

Moreover, treating AML can result in a decrease in size of an area or zone of cellular proliferation, and, in particular, an extramedillary leukemic mass. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating AML can result in a decrease in the number or proportion of cells having an abnormal appearance or morphology (i.e., morphological regression). Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a dactinomycin composition of the disclosure acts selectively on a cancer or precancerous cell but not on a normal cell. Preferably, a dactinomycin composition of the disclosure acts selectively to modulate one molecular target (e.g., RNA/DNA chain elongation by inhibiting ribosome biogenesis) but does not significantly modulate another molecular target (e.g., a cellular repair enzyme). Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A dactinomycin composition of the disclosure can modulate the activity of a molecular target (e.g., a ribosome). Modulating refers to stimulating or inhibiting an activity of a molecular target. Preferably, a dactinomycin composition of the disclosure modulates the activity of a molecular target if it stimulates or inhibits the activity of the molecular target by at least 2-fold relative to the activity of the molecular target under the same conditions but lacking only the presence of said compound. More preferably, a dactinomycin composition of the disclosure modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

Dactomycin

Dactomycin may also be referred to as 2-amino-N,N'-bis (hexadecahydro-2,5,9-trimethyl-6,13-bis(1-methylethyl)-1, 4,7,11,14-pentaoxo-1H-pyrrolo(2,1-I)(1,4,7,10,13)oxatetra-azacyclohexadecin-10-yl)-4,6-dimethyl-3-oxo-3H-phenoxazine-1,9-dicarboxamide, ActD, Actinomycin C1, Actinomycin D; Actinomycin iv, Dactinomicina, Dactinomycin, Dactinomycine, Dactinomycinum, or Meractinomycin. Dactomycin belongs to the class of organic compounds known as cyclic depsipeptides. Cyclic depsipeptides include natural and/or non-natural (i.e., synthetic) compounds having sequences of amino and hydroxy carboxylic acid residues (usually α-amino and α-hydroxy acids) connected in a ring. Amino and hydroxy carboxylic acid residues within Dactomycin may alternate in a repeating pattern.

Dactomycin is a small molecule composed of a two cyclic peptides attached to a phenoxazine that is derived from streptomyces parvullus. Dactomycin binds to DNA and inhibits RNA synthesis (transcription) by specifically interfering with chain elongation of mRNA transcripts. Dactomycin binds strongly but reversibly to DNA molecules. As a result of impaired mRNA production, protein synthesis, ribosome biogenesis and cell division decline after dactinomycin therapy. Because Dactomycin inhibits cell division, it is hypothesized that Dactomycin inhibits the oncogenic cell division present with AML in the bone marrow.

Pharmaceutical Formulations

The disclosure provides pharmaceutical compositions comprising Dactinomycin in combination with at least one pharmaceutically acceptable excipient or carrier.

A "pharmaceutical composition" is a formulation containing a Dactinomycin composition of the disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. Although compositions of the disclosure may be administered by any route, preferred routes of administration include intravenous injection or infusion. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the disclosure is formulated to be compatible with its intended route of administration. Examples of routes of administration include intravenous administration. Solutions or suspensions used for intravenous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A Dactinomycin composition of the disclosure can be administered to a subject in many of the well-known methods currently used for chemotherapeutic treatment. For example, for treatment of cancers, a Dactinomycin composition of the disclosure may be injected into the blood stream. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a Dactinomycin composition to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In a preferred aspect, the disease or condition to be treated is AML.

For any composition of the disclosure, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active Dactinomycin compounds of the disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the Dactinomycin composition in the required amount in an appropriate solvent with one or a combination of ingredients enumerated above, as required, followed by filtered sterilization. Generally, dispersions are prepared by incorporating the active Dactinomycin compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 1 µg/kg per day to about 30 µg/kg per day in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present disclosure are capable of further forming salts. All of these forms are also contemplated within the scope of the claimed disclosure.

As used herein, "pharmaceutically acceptable salts" refer to derivatives of the compounds of the disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the disclosure can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the disclosure can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the disclosure can be delivered in prodrug form. Thus, the disclosure is intended to cover prodrugs of the presently claimed compounds, methods of delivering the same and compositions containing the same. "Prodrugs" are intended to include any covalently bonded carriers that release an active parent drug of the disclosure in vivo when such prodrug is administered to a subject. Prodrugs in the disclosure are prepared by modifying functional groups present in the compound in such a way that the modifications are cleaved, either in routine manipulation or in vivo, to the parent compound. Prodrugs include compounds of the disclosure wherein a hydroxy, amino, sulfhydryl, carboxy or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the disclosure, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

The dosage regimen can be daily administration (e.g. every 24 hours) of a compound of the disclosure. The dosage regimen can be daily administration for consecutive days, for example, at least two, at least three, at least four, at least five, at least six or at least seven consecutive days. Dosing can be more than one time daily, for example, twice, three times or four times daily (per a 24 hour period). The dosing regimen can be a daily administration followed by at least one day, at least two days, at least three days, at least four days, at least five days, or at least six days, without administration. For example, a compound of the disclosure is administered at least once in a 24 hour period, then a compound of the disclosure is not administered for at least six days, then a compound of the disclosure is administered to a subject in need.

Techniques for formulation and administration of the disclosed compounds of the disclosure can be found in *Remington: the Science and Practice of Pharmacy*, 19<sup>th</sup> edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the disclosure are apparent from the different examples. The provided examples illustrate different components and methodology useful in practicing the disclosure. The examples do not limit the claimed invention. Based on the present disclosure the skilled artisan can identify and employ other components and methodology useful for practicing the disclosure.

EXAMPLES

In order that the disclosure disclosed herein may be more efficiently understood, examples are provided below. It should be understood that these examples are for illustrative purposes only and are not to be construed as limiting the disclosure in any manner.

Example 1: Dactinomycin Treatment of NPM1-Mutated Acute Myeloid Leukemia

Figure 7:
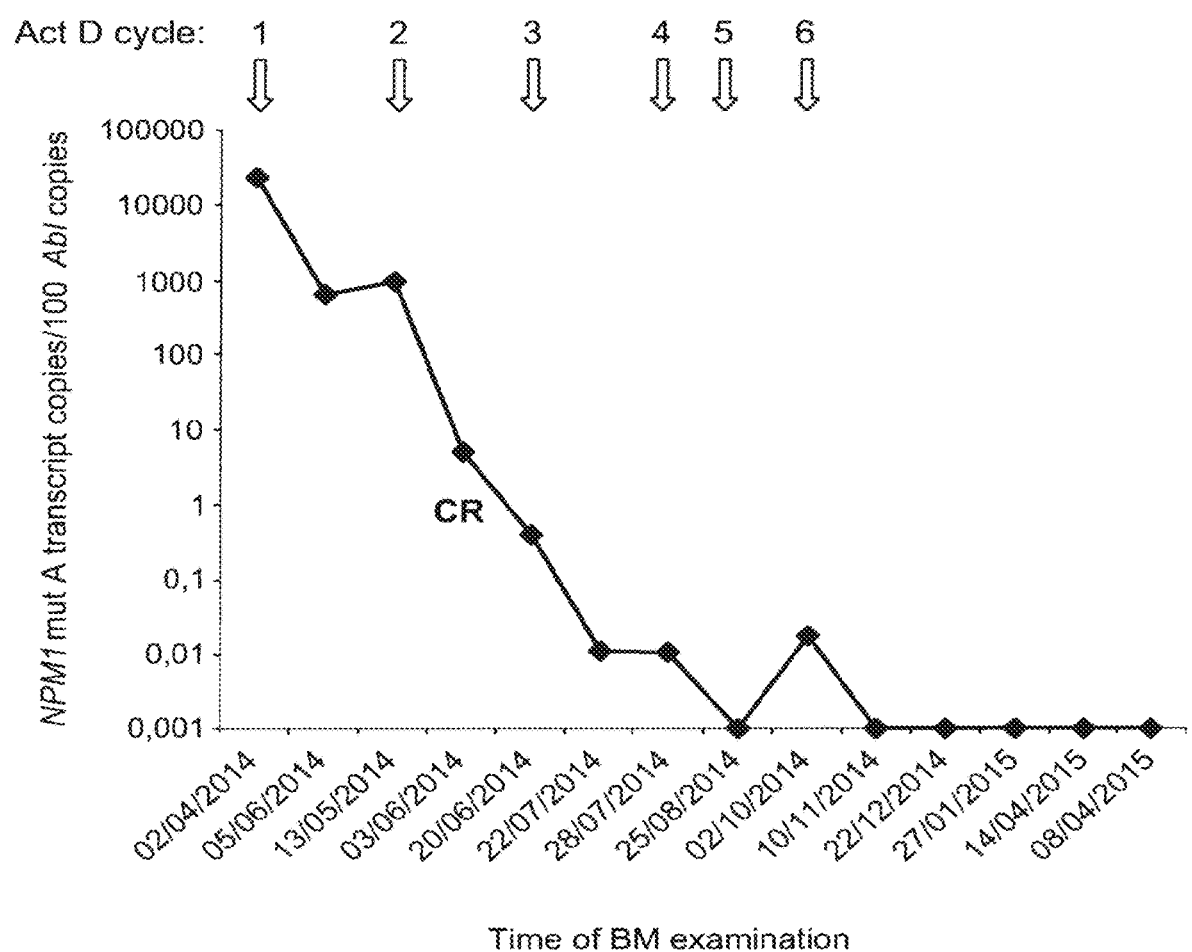
FIG. 7 is a quantitative reverse-transcriptase-polymerase-chain-reaction (RT-PCR) assay for mutant copies of NPM1 in bone marrow samples that shows a progressive reduction in copies during dactinomycin treatment. Negativity for minimal residual disease was achieved after the fourth cycle. Data are presented as the number of copies of NPM1 per 100 copies of Abl. The technical limit of detection is 0.001 copies of NPM1 per 100 copies of Abl. Red arrows indicate when dactinomycin cycles were administered. Complete remission indicates the time when hematologic response was achieved (after two cycles of dactinomycin).

A 60-year-old patient with NPM1-mutated AML without FLT3 internal tandem duplication mutations was treated with dactinomycin. Because dactinomycin lacks cardiotoxicity, a patient was selected for whom intensive chemotherapy was not appropriate owing to a low left ventricular ejection fraction (35%). Leukemia had progressed after an initial single cycle of azacitidine. Therefore, with the patient's consent, dactinomycin was administered as an off-label single agent (approved by the institutional review board at Perugia Hospital), at a dose of 12.5 µg per kilogram of body weight per day for 5 consecutive days, as recommended for low-risk gestational trophoblastic tumors. Morphologic and immunohistochemical complete remission was achieved after two cycles of therapy (FIGS. 1-6). Four more cycles were administered for a total of six cycles, at intervals of 3 to 4 weeks. A quantitative reverse-transcriptase-polymerase-chain-reaction assay for mutant copies of NPM1 showed a molecular complete remission after the fourth cycle (FIG. 7). The patient has now had a morphologic and molecular complete remission lasting 14 months. Adverse events included febrile neutropenia and thrombocytopenia of grade 4 during cycles 1 and 2 (Table 1), grade 2 oral mucositis during cycles 1 through 3, and superficial skin erosions during cycle 2. Cycles 3 through 6 were administered on an outpatient basis, with no need for blood transfusions (Table 1).

The progressive decrease in NPM1 mutant transcripts (until the achievement of negativity for minimal residual disease) is reminiscent of dactinomycin-induced normalization of serum levels of human chorionic gonadotropin in patients with gestational trophoblastic tumors.

Six additional patients with refractory or relapsed NPM1-mutated AML were treated with cycles of dactinomycin at a dose of 15.0 µg per kilogram per day for 5 consecutive days. A hematologic complete remission was achieved in two patients: one (74 years of age) had not had a response to azacitidine, and another (72 years of age) had had a relapse after multiple lines of chemotherapy.

Table 1 shows hematologic toxic effects during dactinomycin treatment. The number of days with a hemoglobin level of less than 8 g per deciliter, severe thrombocytopenia (a platelet count of <20,000 per cubic millimeter), and severe neutropenia (a neutrophil count of <500 per cubic millimeter) are reported for cycles 1 through 6. A total of 8 units of red cells and 4 units of platelets were transfused during cycle 1, and 4 units of red cells and 1 unit of platelets were transfused during cycle 2. No red-cell or platelet transfusions were necessary after cycle 2.

TABLE 1

| Act D Cycle | Number of days with: | | |
|---|---|---|---|
| | Hb <8 g/dl | PLT <20000/mm$^3$ | PMN <500/mm$^3$ |
| 1* | 3 | 13 | 26 |
| 2** | 3 | 2 | 6 |
| 3 | 0 | 0 | 4 |
| 4 | 0 | 0 | 4 |
| 5 | 0 | 0 | 4 |
| 6 | 0 | 0 | 3 |

*8 RBC and 4 PLT units Tasfusions
**4 RBC and 1 PLT units trasfusions

REFERENCES

1. Falini B, Mecucci C, Tiacci E, et al. Cytoplasmic nucleophosmin in acute myelogenous leukemia with a normal karyo-type. N Engl J Med 2005; 352:254-66.
2. Falini B, Gionfriddo I, Cecchetti F, Ballanti S, Pettirossi V, Martelli M P. Acute myeloid leukemia with mutated nucleophos-min (NPM1): any hope for a targeted therapy? Blood Rev 2011; 25:247-54.
3. Cancer Genome Atlas Research Network. Genomic and epigenomic landscapes of adult de novo acute myeloid leukemia. N Engl J Med 2013; 368:2059-74.
4. Burger K, Mühl B, Harasim T, et al. Chemotherapeutic drugs inhibit ribosome biogenesis at various levels. J Biol Chem 2010; 285:12416-25.
5. Osathanondh R, Goldstein D P, Pastorfide G B. Actinomycin D as the primary agent for gestational trophoblastic disease. Cancer 1975; 36:863-6.

What is claimed is:

1. A method for treating acute myeloid leukemia (AML) in a subject in need thereof comprising administering to the subject between 1 and 30 μg/kg/day of dactinomycin, inclusive of the endpoints, wherein the subject did not respond to treatment with another cancer therapy prior to administration of dactinomycin.

2. The method of claim 1, wherein the amount of dactinomycin administered to the subject is between 10 and 20 μg/kg/day, inclusive of the endpoints.

3. The method of claim 1, wherein the amount of dactinomycin administered to the subject is 12.5 μg/kg/day or 15 μg/kg/day.

4. The method of claim 1, wherein dactinomycin is administered once per day.

5. The method of claim 1, wherein dactinomycin is administered for at least one treatment cycle.

6. The method of claim 5, wherein dactinomycin is administered for at least two treatment cycles.

7. The method of claim 5, wherein dactinomycin is administered for six treatment cycles.

8. The method of claim 5, wherein one treatment cycle comprises 5 consecutive days of treatment with dactinomycin.

9. The method of claim 6, wherein an interval between two treatment cycles is at least two weeks.

10. The method of claim 9, wherein the interval is at least four weeks.

11. The method of claim 1, further comprising administering a blood transfusion to the subject, wherein dactinomycin and the blood transfusion are administered simultaneously or sequentially.

12. The method of claim 11, wherein dactinomycin is administered before the blood transfusion.

13. The method of claim 12, wherein the blood transfusion is administered following at least one treatment cycle with dactinomycin.

14. The method of claim 1, wherein dactinomycin is administered systemically.

15. The method of claim 14, wherein dactinomycin is administered by intravenous injection or infusion.

16. The method of claim 1, wherein the subject is at least 50 years of age.

17. The method of claim 1, wherein the subject did not respond to treatment with azacitidine.

18. The method of claim 1, wherein the subject relapsed after treatment with another cancer therapy.

19. The method of claim 6, wherein one treatment cycle comprises 5 consecutive days of treatment with dactinomycin.

20. The method of claim 7, wherein one treatment cycle comprises 5 consecutive days of treatment with dactinomycin.

21. The method of claim 7, wherein an interval between two treatment cycles is at least two weeks.

22. The method of claim 21, wherein the interval is at least four weeks.

23. The method of claim 13, wherein one treatment cycle comprises 5 consecutive days of treatment with dactinomycin.

24. The method of claim 11, wherein the blood transfusion is administered following at least one treatment cycle with dactinomycin.

25. The method of claim 18, wherein the subject relapsed after treatment with azacitidine.

26. The method of claim 1, wherein the amount of dactinomycin administered to the subject is 1 μg/kg/day.

27. The method of claim 1, wherein the amount of dactinomycin administered to the subject is 30 μg/kg/day.

28. The method of claim 27, wherein after treatment with dactinomycin at an initial dose of 30 μg/kg/day of dactinomycin, the amount of dactinomycin administered to the subject is lowered to a maintenance dose.

29. The method of claim 28, wherein the maintenance dose of dactinomycin administered to the subject prevents relapse in the subject.

30. The method of claim 29, wherein the maintenance dose of dactinomycin administered to the subject is 1 μg/kg/day.

31. The method of claim 1, wherein the amount of dactinomycin administered to the subject is between 1 and 30 μg/kg/day of dactinomycin, exclusive of the endpoints.

32. The method of claim 31, wherein after treatment with dactinomycin at an initial dose of between 1 and 30 μg/kg/day of dactinomycin, exclusive of the endpoints, the amount of dactinomycin administered to the subject is lowered to a maintenance dose.

33. The method of claim 32, wherein the maintenance dose of dactinomycin administered to the subject prevents relapse in the subject.

34. The method of claim 33, wherein the maintenance dose of dactinomycin administered to the subject is 1 μg/kg/day.

* * * * *